US009470625B1

(12) United States Patent
Wang et al.

(10) Patent No.: US 9,470,625 B1
(45) Date of Patent: Oct. 18, 2016

(54) METHOD OF EXAMINING PURITY OF DENDRIMERS

(71) Applicant: NATIONAL CHUNG CHENG UNIVERSITY, Chia-Yi County (TW)

(72) Inventors: Shau-Chun Wang, Chia-Yi County (TW); Hui-Yu Tseng, Taichung (TW); Chai-Ling Kao, Kaohsiung (TW)

(73) Assignee: National Chung Cheng University, Chai-Yi County (TW)

( * ) Notice: Subject to any disclaimer, the term of this patent is extended or adjusted under 35 U.S.C. 154(b) by 13 days.

(21) Appl. No.: 14/723,790

(22) Filed: May 28, 2015

(51) Int. Cl.
GO1N 21/00 (2006.01)
GO1N 21/47 (2006.01)
GO1N 21/49 (2006.01)

(52) U.S. Cl.
CPC .......... G01N 21/4785 (2013.01); G01N 21/49 (2013.01)

(58) Field of Classification Search
CPC ........ B01D 15/08; C07H 15/04; C12Q 1/68; G01N 33/00; G01N 21/00; C08L 67/04; C07F 7/08; C09J 7/02
See application file for complete search history.

(56) References Cited

U.S. PATENT DOCUMENTS 5,269,937 A * 12/1993 Dollinger ........... G01N 15/0205
204/452
7,205,428 B2 4/2007 Miki et al.

2002/0031773 A1* 3/2002 Ammon, Jr. ....... G01N 23/2258
435/6.12
2009/0005528 A1* 1/2009 Fujisawa ............... C07F 7/0854
526/279
2015/0132512 A1* 5/2015 Krishnaswamy ........ C08J 3/246
428/35.2
2015/0225439 A1* 8/2015 Rendle ................. C07C 229/06
424/451
2016/0096980 A1* 4/2016 Wieneke ................. B32B 37/26
428/355 BL

FOREIGN PATENT DOCUMENTS

TW    I314565    7/1992
TW    I319767    7/1992
TW    I385193    12/2004

* cited by examiner

Primary Examiner — Tarifur Chowdhury
Assistant Examiner — Jamil Ahmed
(74) Attorney, Agent, or Firm — Rosenberg, Klein & Lee

(57) ABSTRACT

A method of examining the purity of dendrimers is revealed. It comprises steps of measuring a light scattering intensity of a set of pure standards having a specific molecular weight with a static laser light scattering detector by use of flow injection polymer analysis; establishing a scaling relation by doing a regression of a ratio of the light scattering intensity per concentration (I/c) against molecular weight (M.W.); measuring the light scattering intensity of a dendrimer to be tested having the same unit and surface-modified functional group as the set of pure standards, and examining the purity of the dendrimer to be tested according to the scaling relation.

8 Claims, 6 Drawing Sheets

METHOD OF EXAMINING PURITY OF DENDRIMERS

BACKGROUND OF THE INVENTION

1. Field of the Invention

The present invention relates to a method of examining the purity of dendrimers, especially for examining whether a dendrimer to be tested is pure or impure according to a scaling relation established by a relation of light scattering intensity per concentration (I/c) proportional to molecular weight (M.W.) based on the Debye equation.

2. Description of Related Art

Dendrimers typically represent a spherical three-dimensional or "tree-like" morphology, comprising a core, repeat branched units emanating from the core, and functional groups on the surface. Due to their characteristic of low viscosity, high solubility, and non-crystalline, dendrimers are widely used. For instance, Taiwan patent No. I314565, issued on $11^{st}$ Sep. 2009, has disclosed a method for producing a flawless and pure dendrimer which can be used as various high-performance materials in fields of chemistry, medicine, and electronics industry. Moreover, Taiwan patent No. I385193, Taiwan patent No. I319767, and U.S. Pat. No. 7,205,428, have disclosed applications of dendrimers in macromolecular materials and semiconductor materials, and indicated preference for using dendrimers with high purity (e.g. Taiwan patent No. I385193, revealing that luminescence properties of LED may be affected by purity of dendrimers). Although purity of dendrimers is known to play an important role in the use of materials, there is still in lack of an effective method for examining the purity of dendrimers.

Some state-of-the-arts analytical technologies have also been employed to characterize the dendrimers, including matrix assisted laser desorption ionization time-of-flight mass spectrometry (MALDI-TOF MS) and nuclear magnetic resonance (NMR) spectroscopy. However, these instrument are expensive and with many limitations. The MALDI-MS is only a semi-quantitative method in nature due to the inhomogeneous depositions of assayed compounds on the sample ionization plate. Moreover, to acquire the most accurate spectra, various matrixes are usually needed to survey. In addition, the dendrimer ionization efficiencies are sometimes too low to obtain reproducible mass spectrum. NMR spectrum of organic molecules provides reliable structural information, which ensures that the impurity can be clearly observed when mixture sample is assayed. Nevertheless, the low resolution of NMR spectra of macromolecules leads to the difficulties of signal identification, especially for large size of macromolecules, and the situation gets worse for dendrimers while tracing the progress of preparation.

In an early paper (J. Phys. Chem., 1947, 51, pp 18-32), relation of the light scattering intensity of non-absorbed light passing through solution versus solute concentration has been derived. Regardless the solute homogeneity, the following mathematical formula, known as Debye scattering equation, is applicable to determine the molecular weight of a polymer.

$$H(c/I)=1/M.W.+2B \cdot c$$

where the c, I, and M.W. represent the solute concentration, the intensity of scattering light, and polymer molecular weight, respectively, and H and B are two constants. In a dilute solution, where the second order term of concentration is negligible, the ratio of scattering light intensity to solute concentration I/c is directly proportional to polymer molecular weight (M.W.). When H is characterized using a standard polymer solution, the measured ratio of light scattering intensity to concentration of a polymer solution, I/c is able to determine the molecular weight of polymer samples. However, the dendrimer structures are of a rigid sphere instead of the configuration of long chain polymers such as random coil or rod-like shape. Hence conventional polymer standards, e.g. polyethylene oxide or dextran, are not applicable to calibrate static light scattering (LS) detector to directly determine the molecular weight (M.W.) of dendrimers to ensure the purity of synthetic compounds, especially high generation products. In such a case, the determination of dendrimer molecular weight (M.W.) to examine the purity of dendrimers remains challenging.

SUMMARY OF THE INVENTION

In view of the above-mentioned problems, the object of the present invention is to provide a method of examining the purity of dendrimers, comprises the steps of (A) measuring a light scattering intensity of a set of pure standards having a specific molecular weight with a static laser light scattering detector by use of flow injection polymer analysis; (B) establishing a scaling relation by doing a regression of a ratio of the light scattering intensity per concentration (I/c) on the molecular weight (M.W.) of the set of pure standards; and (C) measuring the light scattering intensity of a dendrimer to be tested having and examining the purity of the dendrimer to be tested according to the scaling relation.

According to an embodiment of the present invention, the generation of the set of pure standards is equal to or less than generation of the dendrimer to be tested, and the dendrimer to be tested has the same unit and surface-modified functional group as the set of pure standards. Accordingly, available dendrimers (standards) with high purity can be used for establish a scaling relation to examine the purity of synthesized dendrimer products, especially of higher generations than the standards.

According to an embodiment of the present invention, the set of pure standards are selected from a group consisting of $4^{th}$ to $7^{th}$ generations of poly (amidoamine) (PAMAM) dendrimers having molecular weight ranging from 14215 Da to 116493 Da.

According to an embodiment of the present invention, the set of pure standards are selected from a group consisting of $4^{th}$ to $7^{th}$ generations of pyridine-modified PAMAM dendrimers having molecular weight ranging from 24134 Da to 197938 Da.

According to an embodiment of the present invention, the light scattering intensities of the dendrimer to be tested and the set of pure standards are measured in a dilute solution.

According to an embodiment of the present invention, the light scattering intensity of the dendrimer to be tested is measured according to a linear regression equation of the scaling relation having correlation coefficient ($R^2$) equal to or greater than 0.985, a deviation from the linear regression equation indicating the dendrimer to be tested is impure.

According to an embodiment of the present invention, the scaling relation is established by a relation of the light scattering intensity per concentration (I/c) proportional to the molecular weight (M.W.) based on the Debye equation.

DETAILED DESCRIPTION OF THE PREFERRED EMBODIMENT

Figure 1:
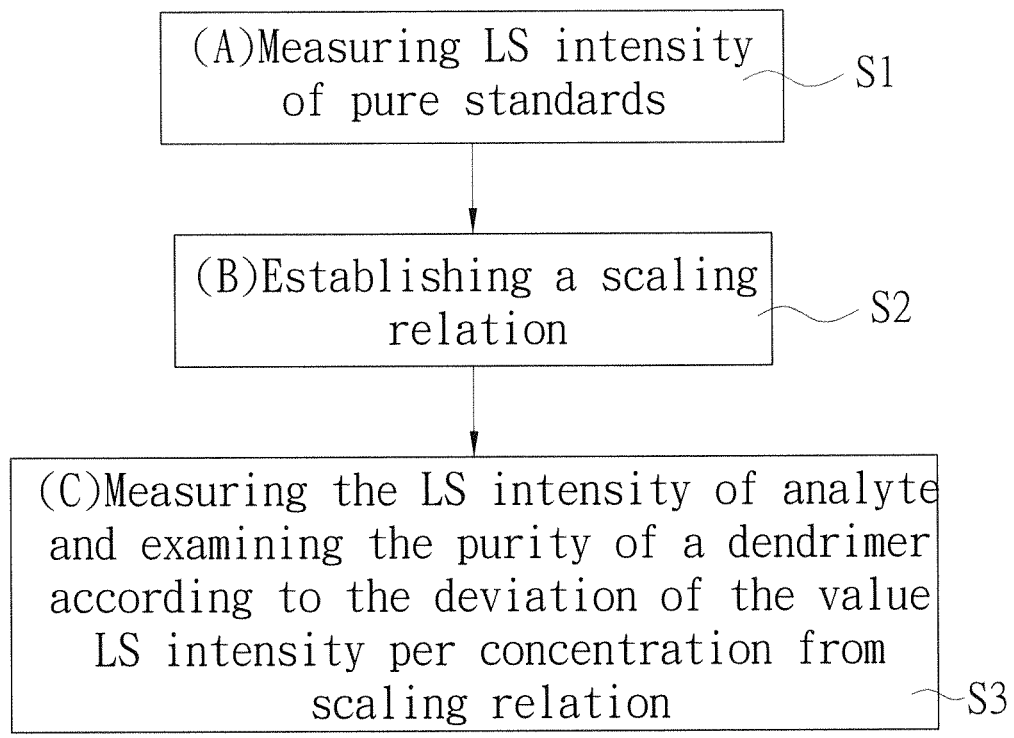
FIG. 1 is a flowchart showing a method for examining the purity of dendrimers according to the present invention.

A flowchart showing a method of examining the purity of dendrimers according to the present invention is revealed in FIG. 1, comprising:

(A) (S1): measuring a light scattering intensity (LS intensity) of a set of pure standards having a specific molecular weight with a static laser light scattering detector by use of flow injection polymer analysis, wherein the set of pure standards are selected from a group consisting of $4^{th}$ to $7^{th}$ generations of PAMAM dendrimers having molecular weight ranging from 14215 Da to 116493 Da or a group consisting of $4^{th}$ to $7^{th}$ generations of pyridine-modified PAMAM dendrimers having molecular weight ranging from 24134 Da to 197938 Da;

(B) (S2): establishing a scaling relation by doing a regression of a ratio of the light scattering intensity per concentration (I/c) on the molecular weight (M.W.) of the set of pure standards; and (C) (S3): measuring the light scattering intensity of a dendrimer to be tested and examining the purity of the dendrimer to be tested according to the scaling relation; for instance, according to a linear regression equation of the scaling relation having correlation coefficient ($R^2$) equal to or greater than 0.985, a deviation from the linear regression equation indicating the dendrimer to be tested is impure. According to the above description, the dendrimer to be tested has the same unit and surface-modified functional group as the set of pure standards. Furthermore, it is worth mentioning that the light scattering intensities of the dendrimer to be tested and the set of pure standards are measured in a dilute solution.

Hereinafter, an exemplary embodiment of the present invention will be described in detail with reference to the accompanying drawings.

Example 1

Establishing a Scaling Relation by Doing the Regression of a Ratio of the Light Scattering Intensity Per Concentration (I/c) on the Molecular Weight (M.W.) of Pure Dendrimers Poly (amidoamine) (PAMAM) dendrimer compounds of fourth to seventh generations (G4-PAMAM to G7-PAMAM) were purchased from Dendritic Co. (Midland, Mich.) and pyridine-modified PAMAM dendrimer compounds of fourth to seventh generations (G4-2PY to G7-2PY) were synthesized and characterized in the followings. The solution of (G:4)-dendri-PAMAM-$(NH_2)_{64}$ (50 mg, 3.5 mmol) in DMF (12 mL) was mixed with pyridine-2-carboxaldehyde (120 mg, 1.12 mmol) and $NaBH(OAc)_3$ (197 mg, 0.9 mmol) at room temperature under continuous nitrogen purging. The resulting solution was mixed with $NaBH(OAc)_3$ (197 mg, 0.9 mmol) and pyridine-2-carboxaldehyde (120 mg, 1.12 mmol) every days until no positive result from nihydrin test. The excess amount of reagents was removed by dialysis (14 k Da cutoff). Finally, the remaining solution contained the desired product (G:4)-dendri-PAMAM-(pyridine)$_{102}$ (G4-2PY) (72 mg, 85%), which was sampled to characterize with $^1$H-NMR spectrometer (400 MHz) in $D_2O$ solvent. The NMR spectrum has the following chemical shift features, 8.66 (d, J=4 Hz, 102 H); 8.42 (t, J=8 Hz, 102 H); 7.97 (d, J=8.0 Hz, 102 H); 7.87 (t, J=8 Hz, 102 H); 4.23 (s, 204 H); 3.56~3.31 (m, 714 H); 2.82~2.72 (m, 372 H). The PDI value of this purified product (G4-2PY) was estimated as 1.14 by using its chromatographic peak recorded with a UV detector (254 nm) eluted from a GPC column (TSK G2000; 7.5×300 mm; 10 μm size) and using the mobile phase solution of 50% methanol and 50% water with 0.1% TFA at flow rate of 1 mL/min. Moreover, pyridine-modified PAMAM dendrimers of the other generations (G5-2PY to G7-2PY) were prepared by similar procedures. The $^1$H-NMR spectra of these products (G5-2PY to G7-2PY) were found to contain similar chemical shift features too. The PDI values of these pure G5, G6, and G7 pyridine-modified PAMAM dendrimers (G5-2PY, G6-2PY, and G7-2PY) were estimated as 1.15, 1.04, and 1.02, respectively. The synthesized dendrimers were dissolved in deionized water to prepare stock solution (3 mg/mL) and kept at 4° C.

As shown in Table 1 and Table 2, the calculated molecular weights of PAMAM dendrimers (G4-PAMAM to G7-PAMAM) and the pyridine-derived PAMAM dendrimers (G4-2PY to G7-2PY) range from 14215 to 116493 Da and from 24134 to 197938 Da, respectively.

TABLE 1

PAMAM dendrimer

| Generation (Gn) | Surface groups | Molecular weight (Da) |
|---|---|---|
| G4 | 64 | 14215 |
| G5 | 128 | 28826 |
| G6 | 256 | 58048 |
| G7 | 512 | 116493 |

TABLE 2

Pyridine-modified PAMAM dendrimer

| Generation (Gn) | Surface groups | Molecular weight (Da) |
|---|---|---|
| G4 | 64 | 24134 |
| G5 | 128 | 47481 |
| G6 | 256 | 97178 |
| G7 | 512 | 197938 |

The refraction index (RI) detector and static laser light scattering (LS) detector equipped in the multiplex detector system (TDA 302; American Polymer Standard Corporation) were calibrated with pollulan standard (P200; M.W. 212 kDa) solution injected into gel permeation chromatography (GPC) column and were eluted with 0.1% trifluoroacetic acid (TFA) mobile phase solution, which was delivered using Malvern's pump (VE 1122). The chromatograms of P200 standard acquired with right angle laser LS detector illuminated at 670 nm and RI to detector maintained at 30° C. were input into Malvern's OmniSEC 4.6 software package to calibrate instrument parameters by setting the standard's M.W. The synthetic dendrimer sample solution (100 µL) of PAMAM ranging from the fourth to seventh generations and their pyridine derivatives were directly injected into the TDA302 detector without using GPC column. The carrier solution 0.1% TFA solution pumped the injected sample through the detector at the flow rate of 0.4 mL/min and temperature of 30° C. to acquire the right angle LS flow injection signals of each sample for 15 min.

Figure 2:
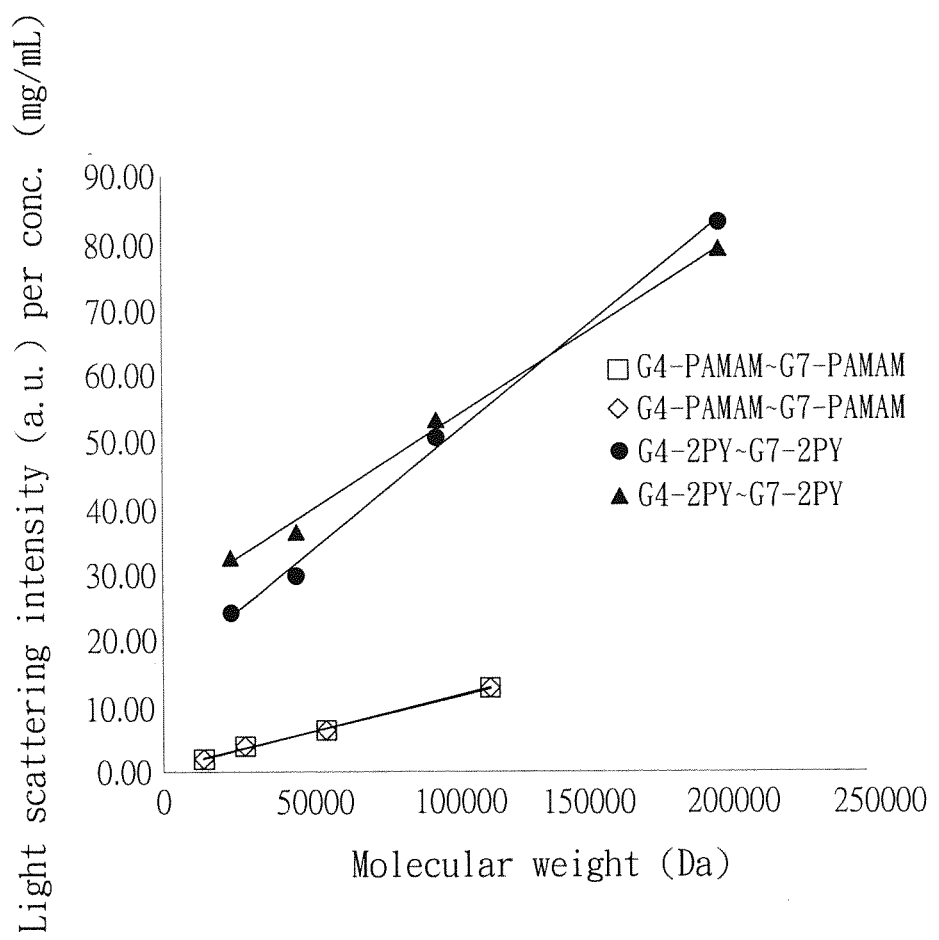
FIG. 2 is a diagram showing linear scaling relation curves of light scattering intensity per concentration (I/c) versus molecular weight (M.W.) of pure dendrimers.

FIG. 2 is a diagram showing linear scaling relation curves of light scattering intensity per concentration (I/c) versus molecular weight (M.W.) of pure dendrimers. When the data of LS intensities per concentration of PAMAM dendrimers of the fourth to the seventh generations (G4-PAMAM to G7-PAMAM) are plotted versus their M.W., these two linear curves prove the scaling relation is valid. The correlation coefficients of these two lines are 0.998 and 0.9964, respectively. The linear curves of the pyridine-modified PAMAM dendrimers of the fourth to the seventh generations (G4-2PY to G7-2PY) data also show the validity of this scaling relation. The correlation coefficients of these two lines are 0.9965 and 0.996, respectively.

Example 2

Figure 3:
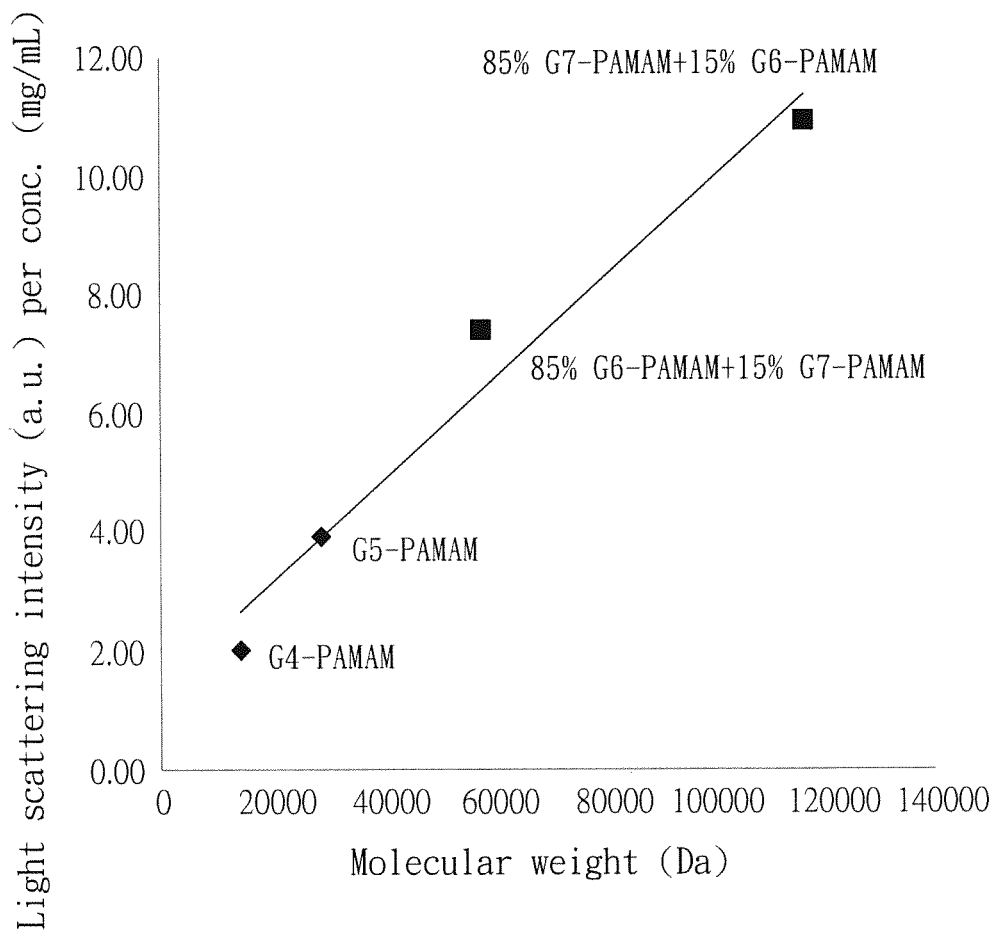
FIG. 3 is a diagram showing linear scaling relation curves of light scattering intensity per concentration (I/c) versus molecular weight (M.W.) of artificial impure PAMAM mixtures.

Examining a Scaling Relation by a Ratio of the Light Scattering Intensity Per Concentration (I/c) Versus the Molecular Weight (M.W.) of Artificial Impure Mixtures The artificial impure mixtures of PAMAM were made of the two consecutive generations. The impure solution of the sixth generation (G6-PAMAM) was prepared by spiking with the seventh generation (G7-PAMAM) sample in the ratio of 85:15. Similarly, the impure solution of the seventh generation (G7-PAMAM) was spiked with the sixth generation (G6-PAMAM) sample in the same ratio. When the data of scattering intensities per concentration using these artificial impurity samples (85% G6-PAMAM with 15% G7-PAMAM and 85% G7-PAMAM with 15% G6-PAMAM) were plotted in FIG. 3 along with the data of pure standards of the fourth and the fifth generations (G4-PAMAM and G5-PAMAM), the scaling relation linearity obviously became less reliable. The correlation coefficient decreased to 0.9652. When the doping amount of the other generation sample increased, the linearity also more deteriorated. For instance, the correlation coefficient decreased to 0.93 when the spiking ratios increased to 70:30 (data not shown).

Figure 4:
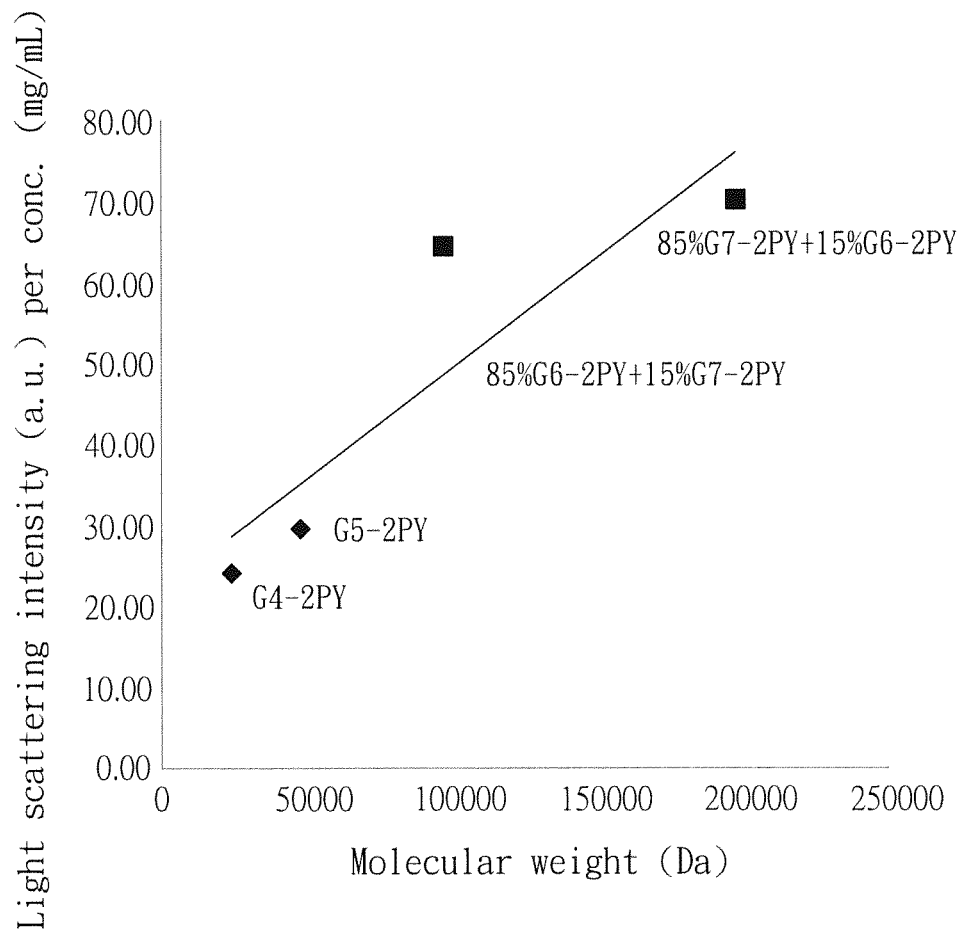
FIG. 4 is a diagram showing linear scaling relation curves of light scattering intensity per concentration (I/c) versus molecular weight (M.W.) of artificial impure pyridine-modified PAMAM mixtures.

Furthermore, the correlation coefficients of the linear scaling relation decreased even more significantly in using pyridine derivatives (pyridine-modified PAMAM dendrimers of the fourth to the seventh generations). The impure solution of the sixth (G6-2PY) was also spiked with the seventh (G7-2PY) generations in the ratio 85:15. Similarly, the impure solution of the seventh generation (G7-2PY) was spiked with the sixth generation (G6-2PY) sample in the same ratio. When the data of scattering intensities per concentration using these artificial impurity samples (85% G6-2PY with 15% G7-2PY and 85% G7-2PY with 15% G6-2PY) were plotted in FIG. 4 along with the data of pure standards of the fourth and the fifth generations (G4-2PY and G5-2PY), the scaling relation linearity obviously became less reliable. The correlation coefficient was only 0.81. The validity of linear relation was clearly influenced. When the spiking ratio increased to 70:30, the linearity barely remained, of which the correlation coefficient was down to 0.69 (data not shown).

The above results indicate that presence of artificial impure dendrimers mixtures causes a deviation from the linear regression equation and makes the scaling relation linearity become less reliable. Accordingly, the pure dendrimers (standards) with unknown molecular weight can be used for establish a scaling relation to determine the purity of synthesized dendrimer products, especially of higher generations than the standards.

Example 3

Figure 5:
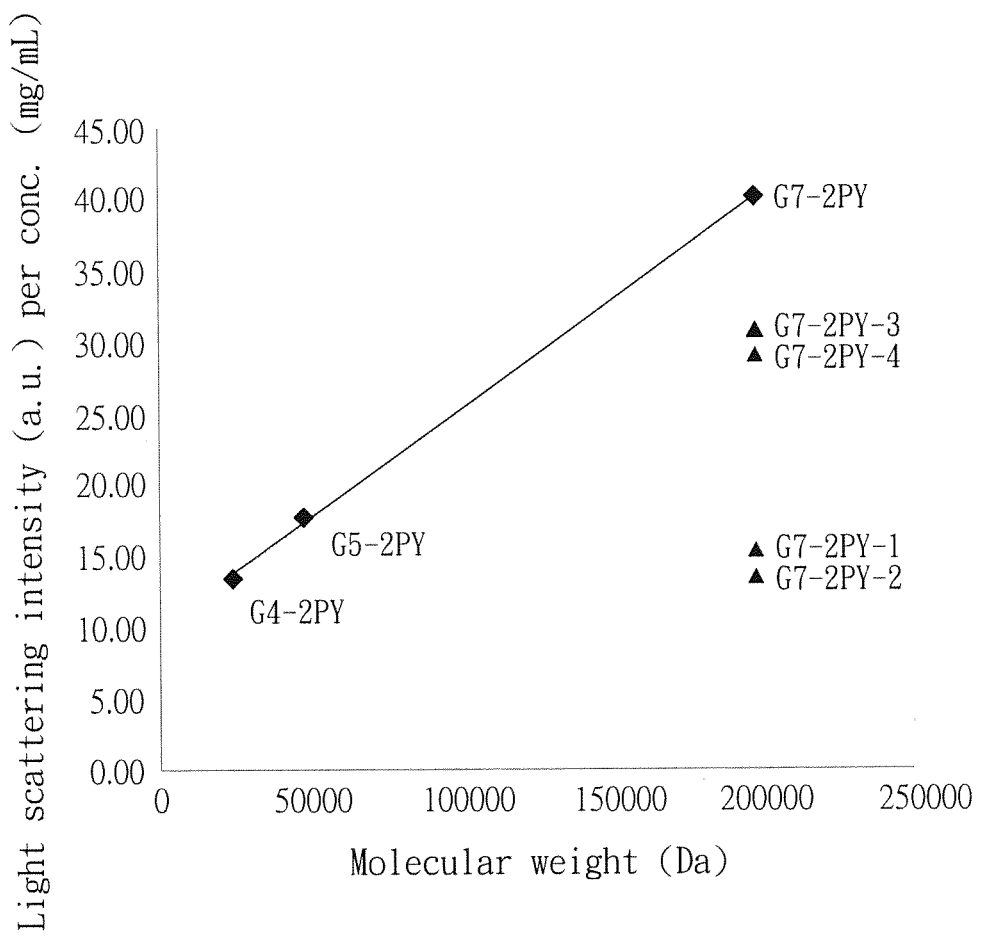
FIG. 5 is a diagram showing deviation of impurity data points from a scaling relation of light scattering intensity per concentration (I/c) versus molecular weight (M.W.) of pure dendrimers.

Examining Data Deviations of Raw Synthesized Dendrimers Products with Incomplete Purifications The raw synthesized products of pyridine modified PAMAM dendrimer without complete reaction derived from PAMAM of the same generation are also used to examine the validity of the linear scaling relation. First, the starting materials of G7-PAMAM dendrimers were incubated with pyridine to produce pyridine-modified PAMAM dendrimers (G7-2PY) at the following reaction times, 6, 9, 15, and 20 days, respectively. Then the LS intensities of solutions containing incompletely converted PAMAM's pyridine derivatives of the seventh generation were measured. In FIG. 5, the LS intensities per concentration of these impure samples synthesized at different reaction times, 6, 9, 15, and 20 days were plotted (respectively labeled with G7-2PY-1, G7-2PY-2, G7-2PY-3, and G7-2PY-4). The linear scaling relation line established with the purified compounds of the fourth, fifth, and the seventh generations (G4-2PY, G5-2PY, and G7-2PY) was also plotted in FIG. 5. The data of impure samples in FIG. 5 show that a general trend to gradually approach the scaling relation line as product conversion time increased.

Figure 6:
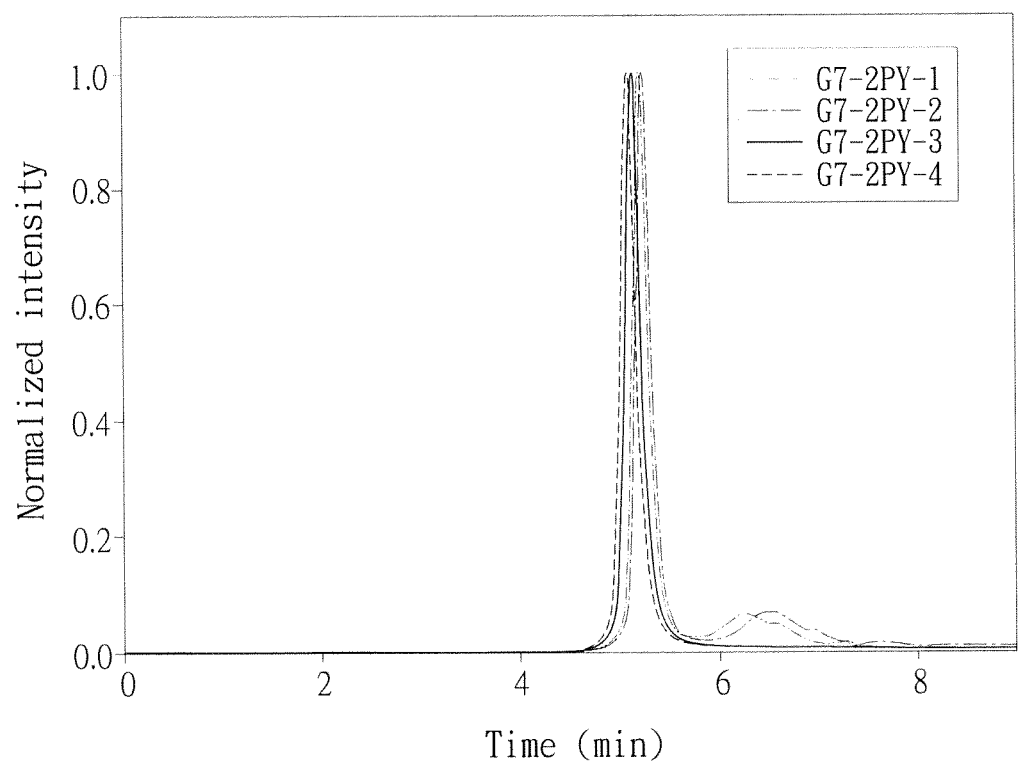
FIG. 6 is a diagram showing UV absorbance chromatograms of incompletely converted pyridine-modified PAMAM dendrimers.

Compared with the results obtained with GPC peaks, the deviation degrees of impure samples are much less sensitive with the separation chromatograms and polydispersity index (PDI) values A diagram showing UV absorbance chromatograms of incompletely converted pyridine-modified PAMAM dendrimers in Example 3 is revealed in FIG. 6. The peaks of remaining non-converted PAPAM were clearly seen in the GPC chromatograms due to short reaction times, of which the traces were 6-day (G7-2PY-1) and 9-day (G7-2PY-2) reaction time samples, whereas the peaks of remaining non-converted PAPAM of 15-day (G7-2PY-3) and 20-day (G7-2PY-4) reaction time samples were disappeared due to longer reaction time. The PDI values of G7-2PY-3 and G7-2PY-4 estimated with GPC peaks were 1.031 and 1.026, respectively. However, these PDI values indicate that the conversions were not completed yet because the PDI value of pure compound (G7-2PY), 1.02, was still slightly smaller than that of impure samples. On the other hand, although the I/c ratio values of these two samples (G7-2PY-3 and G7-2PY-4) in FIG. 5 were also closer to the scaling relation, the deviations were still clearly seen, even when the PDI value differences between impure and pure compounds were only about 0.01. Accordingly, the present method indeed has a relatively high accuracy than the traditional methods for determining the purity of the dendrimer to be tested. When the PAMAM dendrimers are converted to their puridine-modified derivatives, the conversion completion can be clearly evaluated by examining the deviations of scattering intensity per concentration (I/c) values from the scaling relation.

According to the above description, in comparison with the traditional technique, a method of examining the purity of dendrimers according to the present invention has the advantages as following:

1. The present method rapidly and accurately evaluate whether a dendrimer to be tested is pure or impure without using expensive equipment such as MALDI-TOF MS and NMR spectrometer. In addition, using the present method many limitations of MALDI-TOF MS and NMR can also be avoided.

2. The present method is straightforward to examine the purity of dendrimers through a scaling relation which is established by using pure standards having generations equal to or less than generations of the dendrimers. Thus, compared to polydispersity index (PDI), the present method determines whether the dendrimers are impurities easily.

What is claimed is:

1. A method of examining the purity of dendrimers, comprises the steps of:
   (A) measuring a light scattering intensity of a set of pure standards having a specific molecular weight with a static laser light scattering detector by use of flow injection polymer analysis;
   (B) establishing a scaling relation by doing a regression of a ratio of the light scattering intensity per concentration (I/c) on the molecular weight (M.W.) of the set of pure standards; and
   (C) measuring the light scattering intensity of a dendrimer to be tested and examining the purity of the dendrimer to be tested according to the scaling relation.

2. As the method claimed in claim 1, wherein generation of the set of pure standards is equal to or less than generation of the dendrimer to be tested.

3. As the method claimed in claim 1, wherein the dendrimer to be tested has the same unit and surface-modified functional group as the set of pure standards.

4. As the method claimed in claim 1, wherein the set of pure standards are selected from a group consisting of fourth, fifth, sixth, and seventh generations of PAMAM dendrimers having molecular weight ranging from 14215 Da to 116493 Da.

5. As the method claimed in claim 1, wherein the set of pure standards are selected from a group consisting of fourth, fifth, sixth, and seventh generations of pyridine-modified PAMAM dendrimers having molecular weight ranging from 24134 Da to 197938 Da.

6. As the method claimed in claim 1, wherein the light scattering intensities of the dendrimer to be tested and the set of pure standards are measured in a dilute solution.

7. As the method claimed in claim 1, wherein the light scattering intensity of the dendrimer to be tested is measured according to a linear regression equation of the scaling relation, a deviation from the linear regression equation indicating the dendrimer to be tested is impure.

8. As the method claimed in claim 1, wherein the scaling relation is established by a relation of the light scattering intensity per concentration (I/c) proportional to the molecular weight (M.W.) based on the Debye equation.

* * * * *